United States Patent [19]

Yamada et al.

[11] Patent Number: 5,374,753

[45] Date of Patent: Dec. 20, 1994

[54] ORGANIC TRANSITION METAL COMPLEX

[75] Inventors: Satoru Yamada; Akihiro Yano, both of Mie, Japan

[73] Assignee: Tosoh Corporation, Shinnanyo, Japan

[21] Appl. No.: 117,288

[22] Filed: Sep. 7, 1993

[30] Foreign Application Priority Data

Sep. 9, 1992 [JP] Japan .................. 4-265526

[51] Int. Cl.$^5$ .................. C07F 17/00; C07F 7/28; C08F 4/44; C08F 110/02
[52] U.S. Cl. .................. 556/11; 556/12; 556/14; 556/27; 556/28; 526/127; 526/160; 526/161; 526/166; 526/352; 502/104
[58] Field of Search .................. 556/11, 12, 14, 27, 556/28; 526/160, 127, 161, 166, 352

[56] References Cited

U.S. PATENT DOCUMENTS 4,607,112  8/1986  Grubbs et al. .................. 556/52
5,171,871  12/1992  Miyashita .................. 556/27

FOREIGN PATENT DOCUMENTS 0367597  5/1990  European Pat. Off. .

OTHER PUBLICATIONS

Makromol. Chem., Rapid Communications, vol. 13, No. 1, Jan. 13, 1992 "Hydrooligomerization of Propene:A 'Fingerprint' of a Ziegler-Natta Catalyst, 2a)" Paolo Corradini et al., pp. 21-24.

Primary Examiner—José G. Dees
Assistant Examiner—Porfirio Nazario-Gonzalez
Attorney, Agent, or Firm—Oblon, Spivak, McClelland, Maier & Neustadt

[57] ABSTRACT

An organometal complex is provided which is represented by the general formula (1) below:

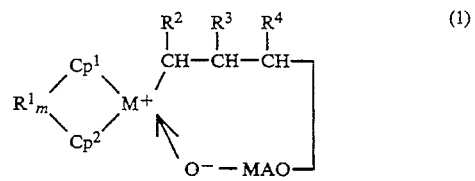

wherein $Cp^1$ and $Cp^2$ are respectively a substituted or unsubstituted cyclopentadienyl group; $R^1$ is a group selected from alkylene groups or arylalkylene groups having 1 to 20 carbons, dialkylsilylene groups, dialkylgermanylene groups, alkylphosphinediyl groups, or alkylimino groups and $R^1$ crosslinking $Cp^1$ and $Cp^2$ together; m is 0 or 1; M is selected from titanium, zirconium, and hafnium; $R^2$, $R^3$, and $R^4$ are independently hydrogen, a hydrocarbon group of 1 to 12 carbons, an alkoxyl group, or an aryloxy group; and MAO is a methylalumoxane group. This organometal complex is capable of producing selectively an olefin polymer without use of any other additional catalyst component.

5 Claims, No Drawings

ORGANIC TRANSITION METAL COMPLEX

BACKGROUND OF THE INVENTION

FIELD OF THE INVENTION

The present invention relates to a novel organometal complex useful by itself for production olefin polymers.

SUMMARY OF THE INVENTION

The present invention intends to provide a novel organometal complex useful by itself for production olefin polymers.

The organometal complex of the present intention is represented by the general formula (1) below:

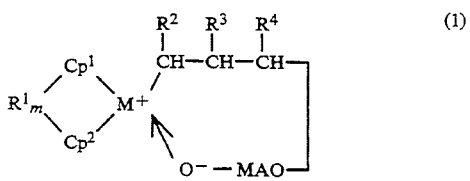

wherein $Cp^1$ and $Cp^2$ are independently a substituted unsubstituted cyclopentadienyl group; $R^1$ is a group selected from alkylene groups or arylalkylene groups having 1 to 20 carbons, dialkylsilylene groups, dialkylgermanylene groups, alkylphosphinediyl groups, or alkylimino groups, and $R^1$ crosslinking $Cp^1$ and $Cp^2$ together; m is 0 or 1; M is titanium, zirconium, or hafnium; $R^2$, $R^3$, $R^4$ and are independently hydrogen, a hydrocarbon group of 1 to 12 carbons, an alkoxyl group, or an aryloxy group; and MAO is a methylalumoxane group.

DETAILED DESCRIPTION OF THE PREFERRED EMBODIMENT

After comprehensive investigation, it was found by the present inventors that a specific organometal complex is useful by itself for production of olefin polymers, and consequently the present invention has been completed.

The compound represented by the general formula (1) above is a novel compound. This compound can be prepared, for example, by reacting an organometallic compound represented by the general formula (2):

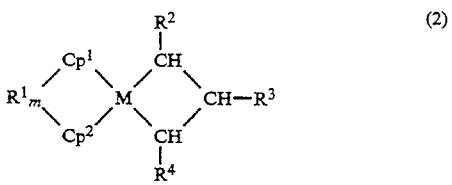

with an alumoxane represented by the general formula (3) or (4):

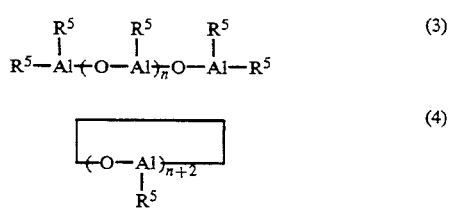

In the formula (2), $Cp^1$ and $Cp^2$ are respectively a substituted or unsubstituted cyclopentadienyl group; $R^1$ is a group selected from alkylene groups or arylalkylene groups having 1 to 20 carbons, dialkylsilylene groups, dialkylgermanylene groups, alkylphosphinediyl groups, or alkylimino groups, and $R^1$ crosslinking $Cp^1$ and $Cp^2$ together; m is 0 or 1; M is selected from titanium, zirconium, and hafnium; $R^2$, $R^3$, and $R^4$ are independently hydrogen, a hydrocarbon group of 1 to 12 carbons, an alkoxyl group, or an aryloxy group; and MAO is a methylalumoxane group. In the formulas (3) and (4), n is an integer of from 4 to 60, and $R^5$ is a hydrocarbon group of 1 to 6 carbons.

The reaction of the compound of the general formula (2) with the compound of the general formula (3) or (4) is conducted generally in the presence of a solvent.

The molar ratio of the compound of the formula (2) to the compound of the formula (3) or (4) is not specially limited. However, the molar ratio of the compound of the formula (2) to the compound of the formula (3) is preferably in the range of from 1:0.5 to 1:100, more preferably from 1:2 to 1:30, and the molar ratio of the compound of the formula (2) to the compound off the formula (4) is preferably in the range of from 1:0.5 to 1:100, more preferably from 1:2 to 1:30.

The solvent for the reaction includes halogenated hydrocarbons such as chloroform and carbon tetrachloride, and aromatic hydrocarbons such as benzene, toluene, and xylene.

The reaction temperature is decided depending on the starting material, the solvent, and other conditions, and is usually selected in the range of from $-50°$ C. to $100°$ C.

The intended compound can be isolated in high purity from the above reaction mixture by recrystallization from a mixed solvent such as toluene-hexane.

The structure of the compound of the present invention can be identified by investigation of reactivity thereof with deuterium chloride.

Example 1

Synthesis of Methylenebis(cyclopentadienyl)-2phenyltitanacyclobutane Methylalumoxane Complex In a nitrogen-purged Shlenk vessel, was placed 3.0 g of methylbis(cyclopentadienyl)-2-phenyltitanacyclobutane. It was dissolved by addition of 15 ml of toluene. The solution was cooled to $-10°$ C. Thereto 10 equivalents of methylalumoxane (16-met, made by Tosoh-Akzo Co. ) was added and the mixture was allowed to react with stirring with gradual rise of the reaction temperature to room temperature in 10 hours. Further the resulting red solution was heated with stirring to $50°$ C. in 3 hours. The reaction mixture was cooled to room temperature. Thereto 10 ml of hexane was added to form immediately a reddish brown solid. The solid was collected by filtration, and recrystallized from a mixed solvent of toluene/hexane (1:2 by volume ratio). The resulting reddish brown complex was dried under high vacuum to obtain 1.7 g of reddish brown complex.

The obtained complex was confirmed to be methylenebis(cyclopentadienyl)-2-phenyltitanacyclotbutane/methylalumoxane complex by formation of 1-phenylpropane-1,3-$d_2$ and 1-phenylpropylene-3-d by reaction of the complex with deuterium chloride (DCl) at $-20°$ C.

Example 2

In a nitrogen-purged Shlenk vessel, was placed 3 mg of methylenebis(cyclopentadienyl)-2-phenyltitanacyclobutane/methylalumoxane complex, and 10 ml of toluene was added thereto to dissolve the complex. Ethylene was bubbled into the resulting red solution of the complex at room temperature. The bubbling was continued for 10 minutes to form white precipitate in the solution. Thereby bubbling of ethylene was stopped to discontinue the reaction. The reaction mixture was poured into 100 ml of a hydrochloric acid-methanol solution. The formed polyethylene was dried in vacuo to obtain 0.34 g of polyethylene.

Example 3

In a nitrogen-purged Shlenk vessel, was placed 0.0042 mmol of methylenebis(cyclopentadienyl)-2-phenyltitanacyclobutane/methylalumoxane complex, and 10 ml of toluene was added thereto to dissolve the complex. 10 ml of styrene was added to this red solution. The mixture was stirred for 2 hours, and then heated to 60° C. to proceed the reaction at that temperature for 10 hours. Thereto 1 ml of methanol was added and the suspension was poured into a hydrochloric acid-methanol solution. The formed polystyrene was dried in vacuo to obtain 1.2 g of polystyrene.

The polymer was extracted with methyl ethyl ketone by Soxhlet extraction. As the result, 0.58 g of methyl ethyl ketone-insoluble polystyrene was obtained.

The melting point thereof was 265° C. by DSC measurement. The polymer had pentad rrrr at a content of 97% or higher according to $^{13}$C-NMR structure analysis in o-dichlorobenzene from the peak at 145.5 ppm resulting from syndiotactic structure.

As shown above, the organometal complex of the present invention is capable of producing selectively an olefin polymer without use of any other additional catalyst component.

What is claimed is:

1. An organometal complex represented by formula (1) below:

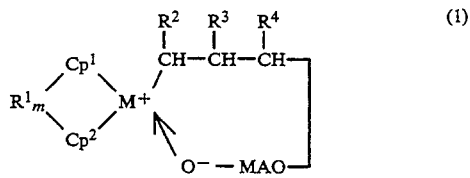

wherein $Cp^1$ and $Cp^2$ are a cyclopentadienyl group; $R^1$ is a group selected from the group consisting of alkylene groups or arylalkylene groups having 1 to 20 carbon atoms, dialkylsilylene groups, dialkylgermanylene groups, alkylphosphinediyl groups, and alkylimino groups, and $R^1$ crosslinking $Cp^1$ and $Cp^2$ together; m is 0 or 1; M is titanium, zirconium, or hafnium; $R^2$, $R^3$ and $R^4$ are independently hydrogen, a hydrocarbon group of 1 to 12 carbon atoms, an alkoxyl group, or an aryloxy group; and MAO is a methylalumoxane group.

2. An organometal compound according to claim 1, wherein M is titanium, $R^2$ is a phenyl group, and $R^3$ and $R^4$ are each hydrogen.

3. An organometal compound according to claim 1, wherein M is titanium, $R^3$ is a methyl group, and $R^2$ and $R^4$ are each hydrogen.

4. A process for producing a polymer of an aromatic vinyl compound, which comprises:
performing the polymerization by bringing said aromatic vinyl compound into contact with an organometal complex as defined in any one of claims 1–3 in an aromatic hydrocarbon.

5. A process for producing a polyethylene, which comprises:
performing the polymerization by bringing ethylene into contact with an organometal complex as defined in any one of claims 1–3 in an aromatic hydrocarbon.

* * * * *